(12) United States Patent
Kim

(10) Patent No.: US 6,345,873 B1
(45) Date of Patent: Feb. 12, 2002

(54) ARTHROSCOPY ORGANIZER SYSTEM

(76) Inventor: Andrew C. Kim, 30213 Del Rey Rd., Temecula, CA (US) 92591

( * ) Notice: Subject to any disclaimer, the term of this patent is extended or adjusted under 35 U.S.C. 154(b) by 0 days.

(21) Appl. No.: 09/470,081

(22) Filed: Dec. 22, 1999

(51) Int. Cl.[7] .............................. A47B 81/00; F16L 3/22
(52) U.S. Cl. ..................... 312/209; 312/223.6; 248/68.1
(58) Field of Search ............................... 312/209, 223.2, 312/223.1, 223.6, 140.4, 249.1, 249.8; 211/89.01, 85.13; 248/68.1; 108/49, 147.19, 147, 25, 28, 60, 93, 92, 97

(56) References Cited

U.S. PATENT DOCUMENTS

| | | | | |
|---|---|---|---|---|
| 1,583,161 A | * | 5/1926 | Malott | 108/93 X |
| 3,341,268 A | * | 9/1967 | Bickford | 312/223.1 X |
| 3,696,920 A | * | 10/1972 | Lahay | |
| 3,819,039 A | * | 6/1974 | Erickson | |
| 3,871,137 A | * | 3/1975 | Grammatico | |
| 4,163,372 A | * | 8/1979 | Frye et al. | 248/68.1 X |
| 4,988,062 A | * | 1/1991 | London | 248/68.1 |
| 5,000,407 A | * | 3/1991 | Juji et al. | |
| 5,660,451 A | * | 8/1997 | Glynn | 312/223.2 |
| 5,690,403 A | * | 11/1997 | Ellison et al. | 312/223.6 |

* cited by examiner

Primary Examiner—James O. Hansen
(74) Attorney, Agent, or Firm—Freling E. Baker; Baker & Eddy

(57) ABSTRACT

An arthroscopy organizing apparatus comprises a generally rectangular box like housing having a front and a back and an upper surface defining a planar support surface, a line holder mounted on the support surface at the back and comprising a resilient elastomeric panel member divided by a plurality of slots into a plurality of resilient holding members defining line receiving and holding areas between adjacent holding members.

9 Claims, 3 Drawing Sheets

ARTHROSCOPY ORGANIZER SYSTEM

BACKGROUND OF THE INVENTION

The present invention relates to an arthroscopy and pertains particularly to an arthroscopy organization system.

Arthroscopic operations are carried out with several instruments or tools that are connected by lines and cord to light source, power source, suction source etc. Currently, because of operating room layout, these instruments are unwrapped from sterile wrapping and hooked up and tested after the patient is brought into the operating room. The connection of the instruments to power, water, vacuum and other such supply sources are in a non-sterile area of the operating room. The instruments themselves are placed on the only sterile area in the operating room, the patient or operating table. This preparation takes a great deal of time while the patient is in the operating room under anesthesia. This preparation is particularly time consuming when problems such as inoperable instruments are found. The instrument must be replaced, repaired or adjusted in preparation for the operation.

The act of connecting the lines and cords to the light source, power source and the suction canister typically takes about four minutes if there are no problems. If there is any problem with the monitor, the pump or any other machine or instrument, much more time is wasted correcting the problem while the patient is under anesthesia. The cords and lines to the instruments are brought over the patient and are tied to drapes over the patients body. They are usually in a disarray and frequently tangled, resulting in time consuming delay in untangling cords and retrieving instrument. There have been cases of patients under anesthesia being burned by the hot instruments placed directly over the patient's abdomen.

Accordingly there is a need for a system to organize the instruments and their lines and cords and to hold the instruments in an organized accessible manner off of and away from the patient.

SUMMARY AND OBJECTS OF THE INVENTION

It is the primary object of the present invention to provide a simple and effective system to organize Arthroscopic instruments and their lines and cord and to hold the instruments in an organized, convenient and accessible manner.

In accordance with a primary aspect of the present invention an arthroscopy instrument organizing apparatus comprises a support member having a substantially planar support surface, and a line holder mounted on said support member and having resilient holding members defining line receiving and holding areas between adjacent holding members.

BRIEF DESCRIPTION OF THE DRAWINGS

The above and other objects and advantages of the present invention will become apparent from the following description and the accompanying drawings wherein.

DETAILED DESCRIPTION OF THE PREFERRED EMBODIMENTS

Figure 1:
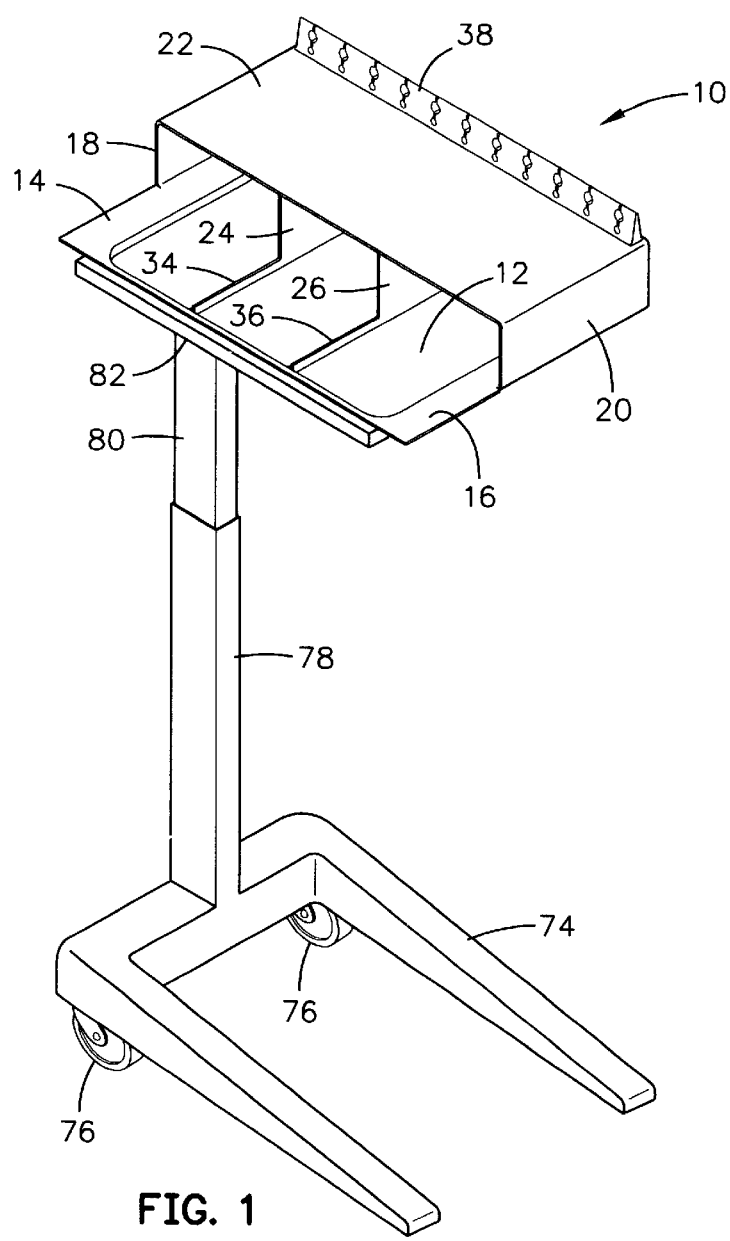
FIG. 1 is a perspective view of an exemplary embodiment of an arthroscopic instrument organizer in accordance with the invention shown mounted on a stand.
Figure 2:
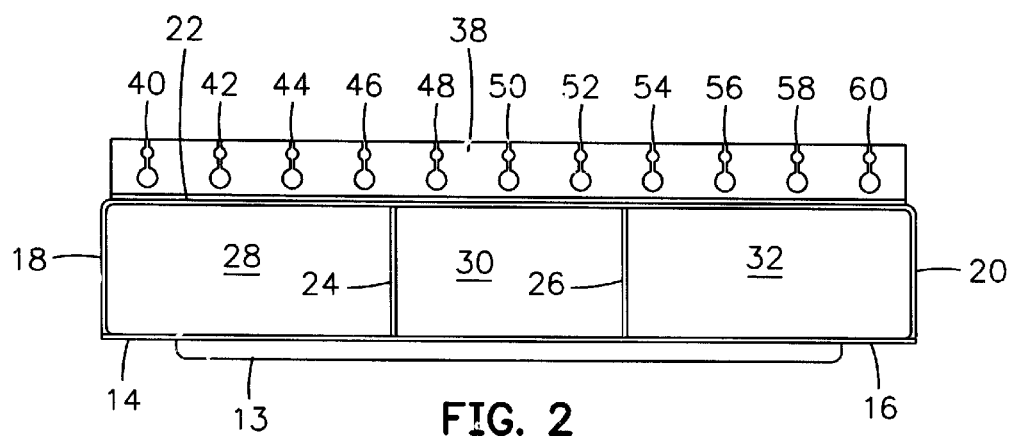
FIG. 2 is a front elevation view of the organizer of FIG. 1.
Figure 3:
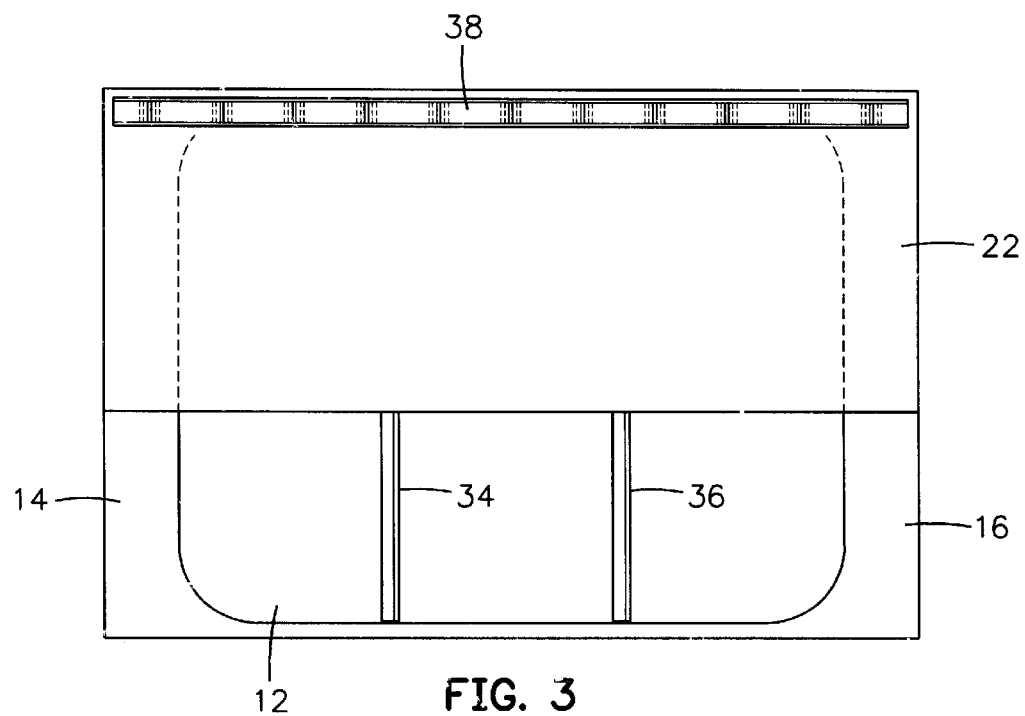
FIG. 3 is a top plan view of the organizer of FIG. 1.

Referring to FIGS. 1–3 of the drawings, an arthroscopy organizing apparatus or system in accordance with one embodiment of the invention is illustrated and designated generally by the numeral 10. The organizing apparatus, as seen in FIG. 1, has a generally box like primary support structure on a tray which is preferably designed the fit on a Mayo stand as shown and will be further explained.

The primary support structure comprises a base support structure in the form of a central tray 12, as shown in FIGS. 2 and 3, adapted to fit a Mayo stand and having extensions 14 and 16 to extend its width beyond that of the width of the Mayo stand to provide greater support area. A box like housing structure having end walls 18 and 20 and a top planar support surface 22 is built on and extends above the tray and forms an open front housing. The box like housing structure is constructed to be about half the depth (fore and aft) of the tray 12 and has an open front to receive instruments. A pair of interior walls or partitions 24 and 26 divide the interior of the housing into three compartments 28, 30 and 32 for receipt and separation of the instruments. A pair of dividers 34 and 36 extend from the ends of the walls across the open tray to the edge thereof to divide the surface thereof into separate support areas.

A line holder and organizer for the system of wires and hoses for the instruments comprises an elongated rail or panel 38 of elastomeric material mounted on top of the housing at or toward the rear thereof. The organizer panel is formed with a plurality of holding slots 40, 42, 44, 46, 48, 50, 52, 54, 56, 58 and 60 for receiving the hoses and lines of the arthroscopy instrument. The slots form adjacent holding members which act to grip the lines and hoses in the slots between them. The slots are each formed with upper and lower holes or rounded portions of different sizes in which the lines and hoses are positioned. The holes are preferably just slightly smaller than the line or hose that is to go therein. This insures that the line will be gripped by the walls of the portion of the slot with sufficient force to be held in place and allow the line or hose to be pulled through.

Figure 6:
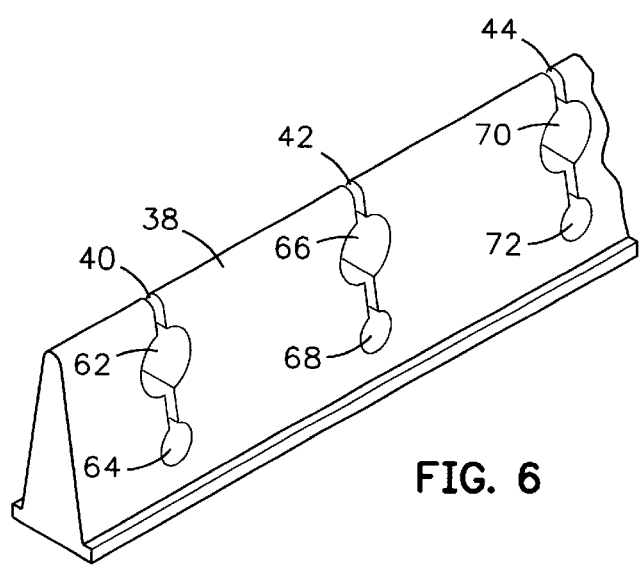
FIG. 6 is a detailed view of a portion of the line holder.

As best seen in FIG. 6, the slots, extend vertically up to and open at the upper edge of the elastic panel. As shown, slots 40, 42, and 44 each have upper and lower holes or enlarged portions 62, 64, 66, 68, 70 and 72 respectively. The holes or enlarged portions of the slots preferably vary in size with a smaller at the top and larger at the bottom to accommodate different size hoses and lines. The elastomeric panel is preferably made from a heat resistant material such as the material currently sold under the mark Teflon.

The organizer of the present invention is designed to fit on a Mayo stand as illustrated in FIG. 1. A Mayo stand is a standard piece of hospital or operating room equipment which as illustrated has a generally u-shaped structural base 74 with wheels or rollers 76 at the four corners thereof for ease of rolling it about. A telescoping vertical post 78 and 80 is attached to and extends upward from one end of the base such that the base can extend underneath a bed or operating table with the post along one side to hold and adjustably position a table top 82 mounted at the upper end of the post. The telescoping post 78 and 80 is vertically adjustable to position it such that the table top 82 extends over and is adjustably positional above a patient on an operating table.

The shelf or table surface 82 is formed with a recess for receiving and holding a tray to prevent it from sliding off. The organizer of the present invention is designed to fit and be supported on a Mayo stand to be accommodated with readily available equipment in an operating room.

Figure 4:
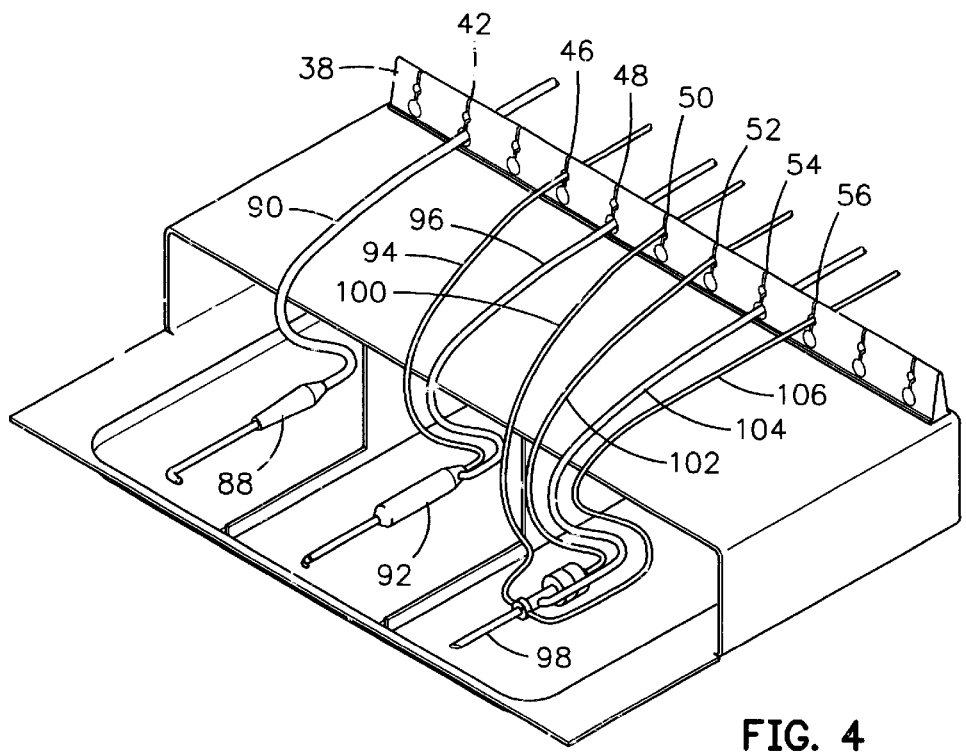
FIG. 4 is a perspective view of the organizer of FIG. 1 showing instruments in place.

In operation with the present invention, the operating room will be set up with a Mayo stand with a sterilized organizer such as FIG. 4 mounted on the stand such as illustrated in FIG. 1. The sterilized instruments may then be taken to the operating room and removed from their packaging and placed on the tray in a manner such as for example as illustrated in FIG. 4. For example as shown in FIG. 4, a thermo-probe 88 is shown placed in the tray in front of compartment 28 and includes a line 90 extending therefrom and extends through and secured in slot 42 of the holder 38. The line 90 may be positioned in either the upper or lower hole of slot 42 as desired. Preferably the line 90 is positioned such that it is slightly gripped by the slot such that sufficient line can be pulled through to enable the surgeon perform the operation.

A second instrument such as a motorized shaver 92 is shown positioned in the center of the tray in front of center compartment 30 and includes two lines 94 and 96 extending and secured in slots 46 and 48. As discussed previously, only sufficient line is pulled through the holder to enable the surgeon to manipulate the instrument to perform his operation.

A scope and cannula 98 is shown positioned in the tray in front of compartment 32 and includes four lines and hoses extending therefrom. As shown, line 100 extends and is gripped in slot 50, line 102 is in slot 52, line 104 is extended into and gripped in slot 54 and line 106 extends through and is gripped in slot 56. It will be apparent that the line or lines from any one of the instruments may be positioned in any selected desirable slot.

The organizing apparatus of FIGS. 1–4 was designed to provide an optimum size to hold the various instruments needed by the surgeon during the surgery. However, it is desirable that the organizer also be sized to fit a flash autoclave, however this is difficult with the arrangement as illustrated. While the illustrated apparatus will fit a flash autoclave when all shelves and racks are removed from the autoclave such is not desirable because of the inconvenience.

Figure 5:
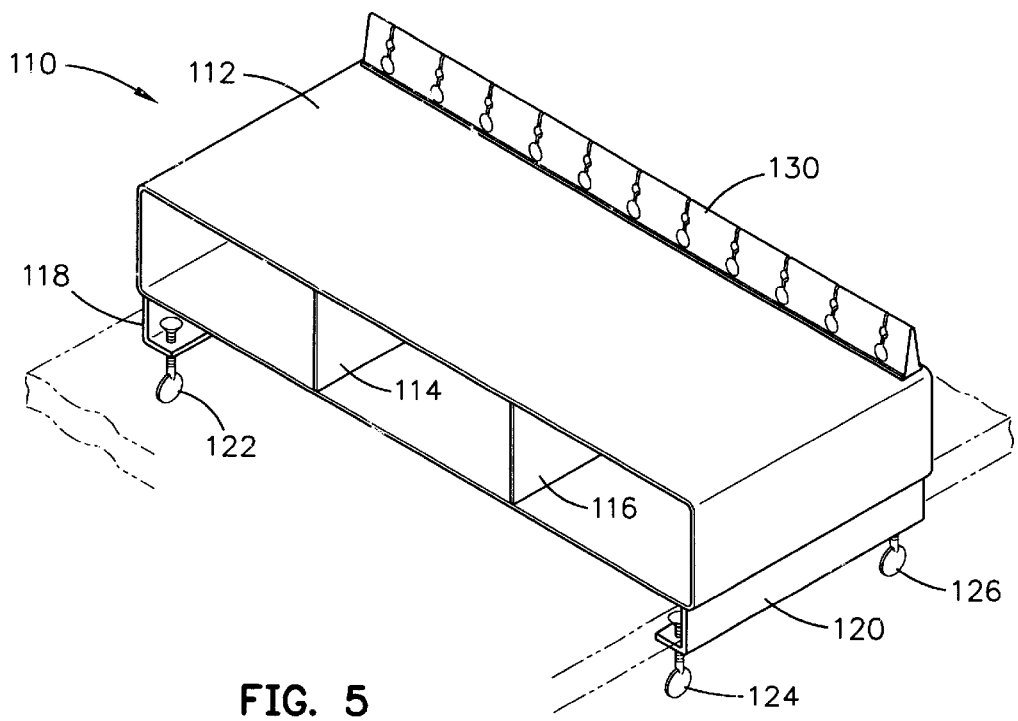
FIG. 5 is a view like FIG. 4 of an alternate embodiment.

Referring to FIG. 5, an apparatus in accordance with the invention is illustrated which is designed to be sized to fit the flash autoclave yet clamp to the typical Mayo stand. As illustrated, the apparatus designed generally by the numeral 110 comprises a box-like housing structure 112 substantially as in the previous embodiment however without the laterally extended tray as in the prior embodiment. The embodiment includes the box-like substantially rigid structure with partitions 114 and 116 dividing the interior thereof into three compartments as in the prior embodiment. The housing as illustrated is provided, by way of example, with a pair of clamps 118 and 120 designed to fit over and clamp to the edges of the shelf or table of a Mayo stand. The clamps include clamping means such as thumbscrews 122, 124 and 126 for gripping and securing it to the Mayo stand table. Other suitable clamping means may be utilized or provided. The apparatus is provided with the line holder 130 with the used slot construction as in the previous embodiment. This line holder has the usual series of slots as in the prior embodiment.

It is apparent that the apparatus of the present invention can be made from many different materials. For example, stainless steel is a preferred material for the housing and tray unit for reuseable units. However, it can be made by molding from any one of known disposable medical grade plastic materials.

While I have illustrated and described my invention by means of specific embodiments, it is to be understood that numerous changes and modifications may be made therein without departing from the spirit and the scope of the invention as shown in the appended claims.

I claim:

1. An arthroscopy organizing apparatus comprising:

an elongated substantially rigid support member having opposite ends and releasable clamps integral with and extending below said support member at said opposite ends for detachable attachment to opposite side edges of a substantially planar support surface; and an elongated line holder mounted on said support member and having a plurality of resilient holding members defining line receiving and holding areas between adjacent holding members.

2. An arthroscopy organizing apparatus according to claim 1 wherein said line holder comprises a resilient elastomeric panel member divided by a plurality of slots into said holding members.

3. An arthroscopy organizing apparatus according to claim 2 wherein at least some of said slots have enlarged areas therein.

4. An arthroscopy organizing apparatus according to claim 1 wherein said line receiving and holding areas comprises a plurality of slots in a resilient elastomeric panel.

5. An arthroscopy organizing apparatus according to claim 4 wherein at least some of said slots have enlarged areas therein.

6. An arthroscopy organizing apparatus comprising:

a support tray having a substantially planar support surface;

a generally rectangular housing on said tray having an open front, a plurality of partitions and an upper surface defining said planar support surface; and a line holder mounted on a rear portion of said upper surface and having resilient holding members defining line receiving and holding areas between adjacent holding members, wherein said tray includes panels aligned with said plurality of partitions.

7. An arthroscopy organizing apparatus according to claim 6 wherein said line receiving and holding areas comprises a plurality slots in a resilient elastomeric panel.

8. An arthroscopy organizing apparatus according to claim 7 wherein at least some of said slots have enlarged areas therein.

9. An arthroscopy organizing apparatus according to claim 6 wherein said apparatus includes clamps adapted to mount on side edges of a tray table.

* * * * *